(12) United States Patent
Seaward et al.

(10) Patent No.: US 7,397,560 B2
(45) Date of Patent: Jul. 8, 2008

(54) SURFACE CONTAMINATION DETECTION

(75) Inventors: Karen L. Seaward, Palo Alto, CA (US); David T. Dutton, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 119 days.

(21) Appl. No.: 11/397,064

(22) Filed: Apr. 4, 2006

(65) Prior Publication Data

US 2007/0229819 A1    Oct. 4, 2007

(51) Int. Cl.
    *G01J 3/443*      (2006.01)
    *G01N 21/73*      (2006.01)
    *G01N 21/94*      (2006.01)

(52) U.S. Cl. ..................... 356/316; 356/237.2
(58) Field of Classification Search ......... 356/313–316, 356/37.22
See application file for complete search history.

(56) References Cited

U.S. PATENT DOCUMENTS

| | | | |
|---|---|---|---|
| 5,537,206 A * | 7/1996 | Akiyoshi et al. | 356/315 |
| 5,705,787 A * | 1/1998 | Karanassios | 219/121.52 |
| 6,184,982 B1 * | 2/2001 | Karanassios | 356/311 |
| 6,441,552 B1 | 8/2002 | Brandenburg et al. | |
| 6,686,998 B2 * | 2/2004 | Gianchandani et al. | 356/316 |
| 6,934,021 B2 * | 8/2005 | Eklin et al. | 356/313 |
| 6,949,741 B2 * | 9/2005 | Cody et al. | 250/288 |
| 7,112,785 B2 * | 9/2006 | Laramee et al. | 250/288 |
| 7,138,626 B1 * | 11/2006 | Karpetsky | 250/288 |
| 7,280,202 B2 * | 10/2007 | Okumura et al. | 356/316 |
| 2005/0162647 A1 * | 7/2005 | Okumura et al. | 356/316 |
| 2005/0195393 A1 * | 9/2005 | Karanassios | 356/316 |

FOREIGN PATENT DOCUMENTS

JP            59019844 A    *    2/1984

OTHER PUBLICATIONS

"PC2000 PC Plug-in Spectrometer" Ocean Optics Inc. (www.oceanoptics.com/products/pc2000.asp).

* cited by examiner

*Primary Examiner*—Gregory J. Toatley, Jr.
*Assistant Examiner*—Bryan Giglio (57) ABSTRACT

A contamination detector in accordance with one embodiment of the invention includes a plasma generation system operable to direct an atmospheric plasma discharge towards a surface. The contamination detector further includes a light capture system to capture light generated by interaction of the atmospheric plasma discharge with the surface. The light capture system guides the captured light to an optical detection system configured to detect a contaminant.

20 Claims, 7 Drawing Sheets

SURFACE CONTAMINATION DETECTION

DESCRIPTION OF THE RELATED ART

Detection of contaminants that may be present upon the surface of an object such as a chemical container has been traditionally carried out using one of several alternative devices and methods. Unfortunately, many of these devices and methods suffer from one or more handicaps. A few examples of such handicaps relate to operational hazards, operational complexity, lack of equipment portability, and lack of equipment versatility.

Elaborating on the aspect of operational hazards, several existing surface contamination detection techniques involve swabbing a surface to obtain a test sample. This process involves direct contact with the contaminant thereby necessitating restrictive handling procedures and protective gear to protect the operator from exposure to the contaminant.

As for operational complexity, several of the traditionally available devices and methods necessitate a high level of operator expertise. For example, in certain instances, it is necessary for the operator to have the ability to perform intricate chemical tests and interpret the results of these tests using complex laboratory instrumentation.

Furthermore, some traditional equipment used for detection of surface contaminants tends to be bulky and cumbersome to operate. The large bulk precludes such equipment from being used in restricted places such as the narrow confines inside a chemical container when testing for the presence of contaminants on the internal surface of the container.

A further handicap of traditional surface contamination detection equipment pertains to a lack of versatility as a result of the equipment being limited to detecting a few specific types of contaminants and not being easily adaptable for detecting a wide variety of contaminants.

Based on the above-mentioned handicaps of existing surface contamination detection technology, an unaddressed need exists in the industry to overcome such deficiencies and inadequacies.

SUMMARY

A contamination detector in accordance with one embodiment of the invention includes a plasma generation system operable to direct an atmospheric plasma discharge towards a surface. The contamination detector further includes a light capture system to capture light generated by interaction of the atmospheric plasma discharge with the surface. The light capture system guides the captured light to an optical detection system configured to detect a contaminant.

Clearly, some alternative embodiments may exhibit advantages and features in addition to, or in lieu of, those mentioned above. It is intended that all such alternative embodiments be included within the scope of the present invention, and be protected by the accompanying claims.

BRIEF DESCRIPTION OF THE DRAWINGS

Many aspects of the invention can be better understood with reference to the following drawings. The components in the drawings are not necessarily to scale. Instead, emphasis is placed upon clearly illustrating the principles of the invention. Moreover, in the drawings, like reference numerals designate corresponding parts throughout the several views.

DETAILED DESCRIPTION

The various embodiments in accordance with the invention generally relate to a contamination detector containing a plasma generation system, a light capture system, and an optical detection system. In one exemplary embodiment, the plasma generation system is used to direct an atmospheric plasma discharge towards a surface under test. The atmospheric plasma discharge makes contact with the surface and generates light having a spectral signature. The light capture system captures the generated light and guides the captured light to the optical detection system. The optical detection system analyzes the spectral signature to detect whether the contaminant is present on the surface.

Figure 1:
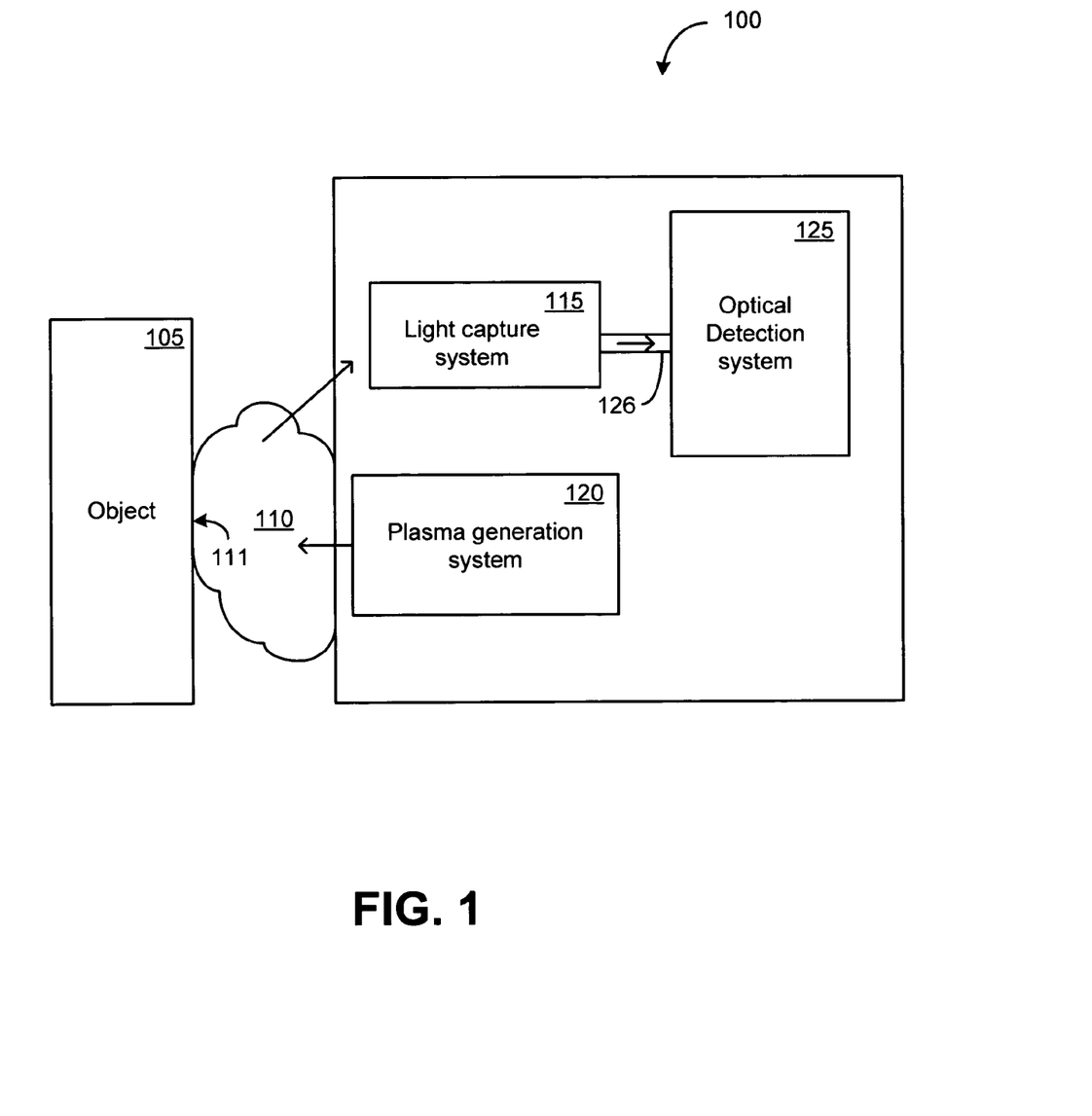
FIG. 1 is a block diagram showing a contamination detector in accordance with the invention.

FIG. 1 is a block diagram showing a contamination detector 100 in accordance with the invention. Detector 100 is used to detect one or more contaminants upon a surface 111 of an object 105. Object 105 represents one of several types of man-made as well as natural objects having one or more surfaces that may be contaminated. A few examples of man-made objects having such surfaces include: a chemical container, a bio-hazardous waste container, a metal wall, a firearm, and a piece of machinery. A few examples of natural objects having surfaces that may be contaminated include wood, plants, fruits, and food produce.

For purposes of illustration, surface 111 of FIG. 1 is shown as an external surface, but it will be understood that surface 111 represents any surface that is accessible for detecting the presence of contaminants. A few examples of surface 111 are: the external surface of a drum, the internal surface of the drum, the internal surface of an oil-well, and the inside wall of a room.

Surface 111 may be coated with any type of organic or inorganic contaminant that is detectable by contamination detector 100. Organic contaminants include all carbon-containing material while inorganic contaminants include various other materials, for example, silicones and certain types of metals.

Contamination detector 100 contains a plasma generation system 120, a light capture system 115, and an optical detection system 125. Plasma generation system 120 generally includes a pair of electrodes and an arrangement whereby a gas, such as air or an inert gas, is passed between the pair of electrodes. A suitable voltage such as a DC voltage, an AC voltage or a pulsed voltage, to name a few, is applied between the electrodes. The amplitude of the applied voltage is selected according to the spacing between the electrodes, with a higher voltage being used for a larger spacing. The applied voltage creates an electric field that initiates plasma breakdown in the gas thereby leading to the atmospheric plasma discharge. The atmospheric plasma discharge is typically expelled out of plasma generation system 120 through a nozzle (not shown) thereby emerging from contamination detector 100 as a shaped discharge slightly above atmospheric pressure. Contamination detector 100 is suitably oriented by an operator (not shown) to direct this discharge towards surface 111.

When an AC voltage or a pulsed voltage is used, the electrodes are typically directly exposed to the generated plasma discharge. Alternatively, electrodes may be encapsulated in a dielectric as in the case of a dielectric barrier discharge (DBD). In alternative embodiments, plasma generation system 120 is implemented in other ways, such as by using a microwave cavity and/or a microwave stripline resonator.

Atmospheric plasma discharge 110 strikes surface 111, interacts with one or more contaminants that may be present upon surface 111, and generates light that has a certain spectrum. The light is captured by light capture system 115 and directed into optical detection system 125 via optical link 126. Optical detection system 125 is used to examine the spectrum of the light and identify a spectral signature that uniquely signifies the presence of a particular contaminant. The detection process will be described below in further detail using FIG. 2.

Figure 2:
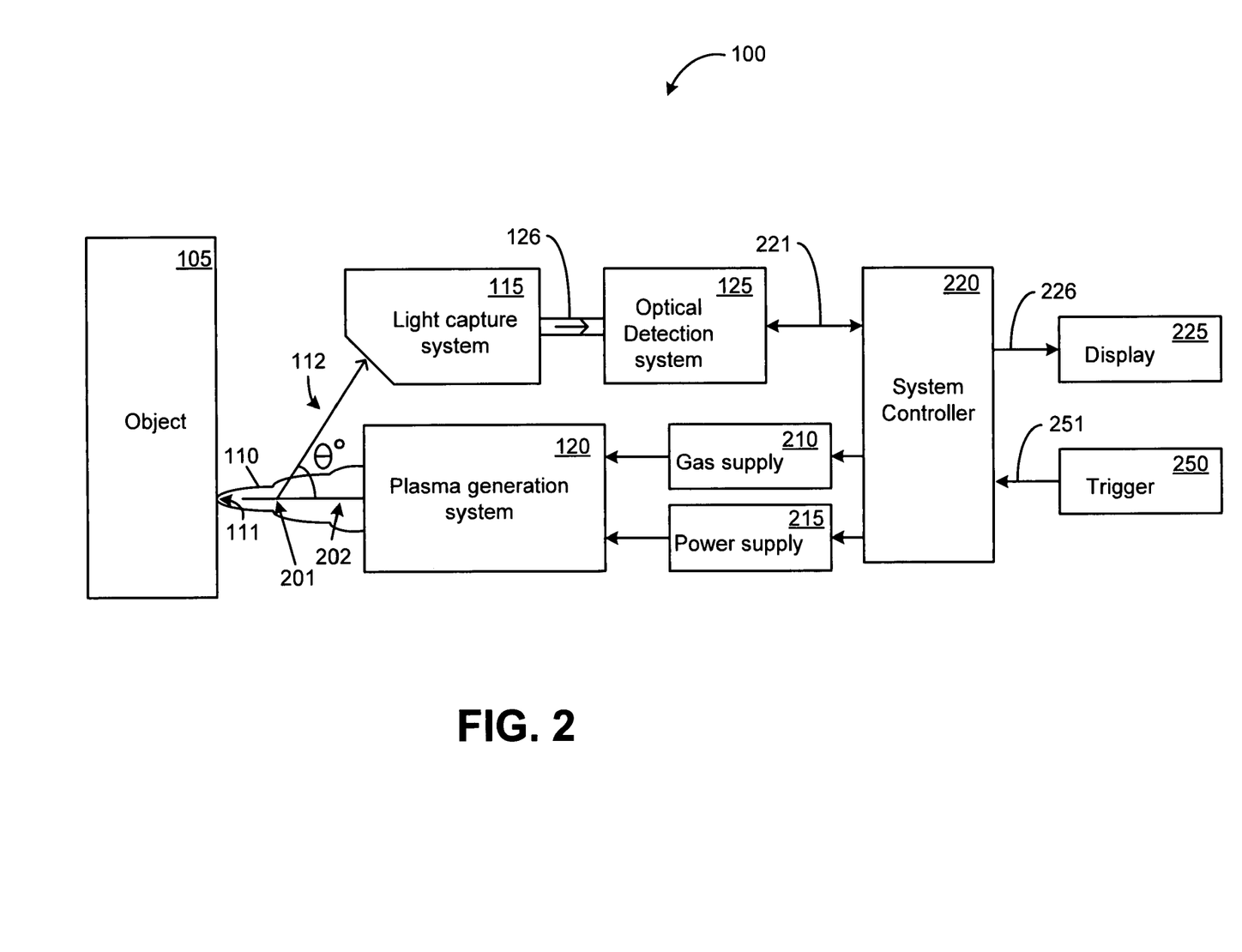
FIG. 2 is a block diagram showing a first exemplary embodiment of the contamination detector of FIG. 1.

FIG. 2 is a block diagram showing a first exemplary embodiment of the contamination detector 100 of FIG. 1. Contamination detector 100 incorporates a plasma generation system 120 that is operable to direct an atmospheric plasma discharge 110 towards surface 111. In this exemplary embodiment, atmospheric plasma discharge 110 is a microdischarge. The term "micro-discharge" is defined in this disclosure as a plasma discharge generated by providing a suitable voltage between contacts spaced apart in an approximate range in the tens to hundreds of micrometers. This exemplary spacing leads to a microdischarge volume ranging from a few nano-liters to a few micro-liters.

Plasma generation system 120 can be implemented using several alternative techniques. One such technique is described by inventor David T. Dutton in U.S. patent application Ser. No. 11/020,377 (Agilent reference number 10041087-1) titled "Systems and Methods for a Contactless Electrical Probe," filed on Dec. 23, 2004 and incorporated by reference.

While atmospheric plasma discharge 110 is shown as being directed towards surface 111 along longitudinal axis 202 normal to surface 111, it will be understood that in other embodiments, plasma discharge 110 is directed towards surface 111 in a direction other than normal to surface 111. The direction is primarily intended to permit atmospheric plasma discharge 110 to make contact with surface 111, while allowing light capture system 115 to be appropriately positioned to capture the light generated by the interaction of atmospheric plasma discharge 110 with surface 111.

Contamination detector 100 further incorporates a light capture system 115 and an optical detection system 125 optically coupled to light capture system 115. Light capture system 115 is arranged to collect light from a specific region 201 inside atmospheric plasma discharge 110. In an alternative embodiment, specific region 201 is located outside atmospheric plasma discharge 110. The light travels from specific region 201 towards light capture system 115 over an optical path having a major axis referred to in this disclosure as light capture axis 112. Specific region 201 is advantageously selected to be close to surface 111 of object 105, thereby ensuring that the captured light has a spectral signature resulting from interaction of atmospheric plasma discharge 110 with surface 111. Light capture axis 112 extends at an angle θ° ($\theta \neq 0$) with respect to the longitudinal axis 202 of the atmospheric plasma discharge 110.

Also included in contamination detector 100 is an optical detection system 125 that is arranged to receive captured light from light capture system 115 and is operable to analyze the spectral signature of the light to detect the presence of a contaminant. Optical detection system 125 may be implemented in various ways depending on various factors such as cost, size, and ease of operation.

In one embodiment, optical detection system 125 is implemented in the form of an optical spectrometer that can be used to analyze several wavelengths simultaneously and consequently detect the presence of several contaminants. Furthermore, the spectrometer is configured to measure the intensity of these wavelengths. The intensity measurement provides a quantitative measure of contamination when one or more contaminants are detected. Commercially-available devices, such as the PC2000 Plug-in Spectrometer, manufactured by Ocean Optics Inc., for example, may be used.

In another embodiment, optical detection system 125 is a low-cost device designed to detect a single contaminant. In this embodiment, optical detection system 125 is implemented in the form of a wavelength filter that isolates light containing certain wavelengths. The isolated light is then coupled to a detector that is specifically adapted to detect these particular wavelengths. The detector is a relatively low-cost device for detecting the presence of certain wavelengths without necessarily measuring the intensity of these wavelengths. When these wavelengths are present, the detector provides an indication that contamination has been detected. Alternatively, when the wavelengths are not present, the detector provides an indication that no contamination has been detected. Consequently, the low cost detector provides a simple presence vs. absence status indication of the contaminant without providing information pertaining to the level of contamination.

Contamination detector 100 also includes a system controller 220 that is operable to control various functions of contamination detector 100. System controller 220 is coupled via link 251 to a trigger 250 and via link 226 to a display 225. When trigger 250 is activated by an operator (not shown), system controller 220 receives a signal via link 251 and, in response, generates one or more signals to initiate atmospheric plasma discharge 110. The initiation process includes providing plasma generation system 120 with a gas from gas supply 210 and a suitable voltage from power supply 215 to energize the electrodes for generating the microdischarge. Gas supply 210 may be replaced by an air supply in certain embodiments.

Atmospheric plasma discharge is expelled out of plasma generation system 120 through a nozzle (not shown) thereby emerging from contamination detector 100 as a shaped discharge. Atmospheric plasma discharge 110 is directed towards surface 111 of object 105. When atmospheric plasma discharge 110 strikes surface 111, a contaminant that may be present on surface 111 affects the spectrum of light generated by the interaction of atmospheric plasma discharge 110 with surface 111. For example, when an organic contaminant is present on surface 111, minute quantities of carbon monoxide and carbon dioxide are generated by the interaction of chemically-reactive oxygen present in the atmospheric plasma discharge and carbon present in the organic contaminant. The carbon monoxide and carbon dioxide contribute a set of unique wavelengths to the spectrum of the light. As a result of the creation of these wavelengths, the light has a unique spectral signature.

The light is coupled into light capture system 115, which transports the light into optical detection system 125 using light transporting techniques such as wave-guiding and total internal reflection. Optical detection system 125 determines the spectral signature of the light to detect the presence of one or more contaminants.

Optical detection system 125 uses various alternative processes to detect one or more contaminants that may be present on surface 111. In a first exemplary process, optical detection system 125 measures the intensity of the light from a set of wavelengths uniquely associated with a particular contaminant. This process is generally applied when the intensity of the light of these wavelengths is stronger and clearly distinguishable relative to the intensity of the light at other wavelengths in the spectral signature. For example, when an organic contaminant is to be detected, optical detection system 125 identifies the presence of a carbon-based compound based on the intensity of the light of a specific set of wavelengths associated with the carbon-based compound.

In a second exemplary process, optical detection system 125 uses a process where the spectral signature of the captured light is compared with a reference spectral signature that is stored in optical detection system 125. This comparison process will be described below in further detail using FIG. 7.

The result of the detection process carried out by optical detection system 125 is communicated to system controller 220 via link 221. System controller 220, in turn, provides a signal that is carried over link 226 to a display 225. Display 225 provides a visual display of the detection results.

Figure 3:
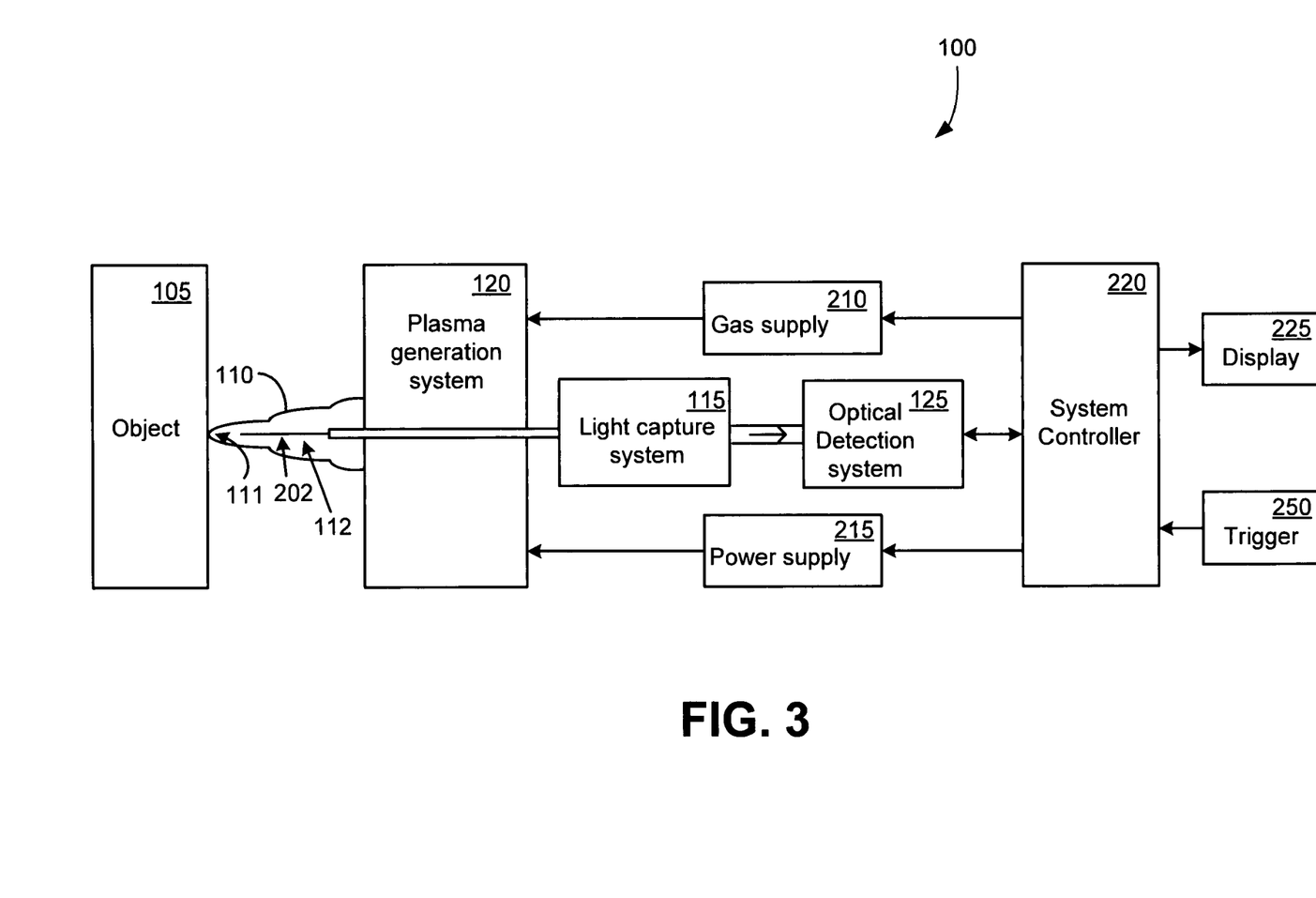
FIG. 3 is a block diagram showing a second exemplary embodiment of the contamination detector of FIG. 1.

FIG. 3 is a block diagram showing a second exemplary embodiment of the contamination detector 100 of FIG. 1. This second exemplary embodiment incorporates several elements of the first exemplary embodiment described above with reference to FIG. 2. However, in contrast to the first embodiment, light capture system 115 is arranged with the light capture axis 112 of light capture system 115 coincident with longitudinal axis 202 of atmospheric plasma discharge 110. Here again, light capture system 115 collects light from inside atmospheric plasma discharge 110.

In an alternative embodiment, light capture axis 112 of light capture system 115 is not necessarily aligned with longitudinal axis 202 of atmospheric plasma discharge 110. Instead, light capture axis 112 of light capture system 115 is parallel to and offset from longitudinal axis 202 of atmospheric plasma discharge 110.

Light capture system 115 incorporates a light focusing system (not shown) that defines a specific region located inside atmospheric plasma discharge 110 from which light is collected. Alternatively, light capture system 115 does not use a light focusing system and instead of collecting light from a specific region, collects light from a broader region inside atmospheric plasma discharge 110.

Figure 4:
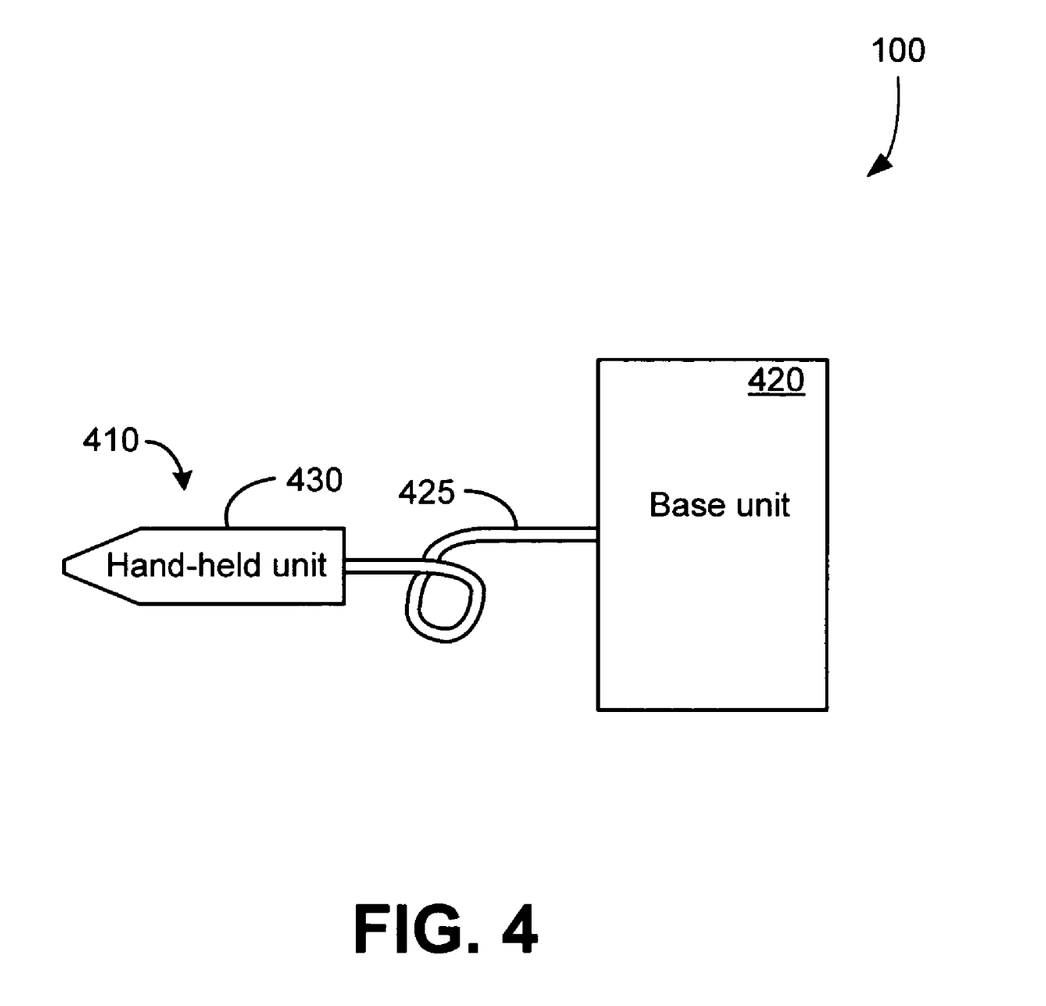
FIG. 4 is a schematic drawing showing a hand-held unit coupled to a base unit in an exemplary implementation of the contamination detector.

FIG. 4 is a schematic drawing showing a hand-held unit 410 coupled to a base unit 420 in an exemplary implementation of contamination detector 100. Hand-held unit 410 includes an enclosure 430 that houses one or more components of contamination detector 100 while base unit 420 includes a second enclosure housing the remaining components, the two units being coupled to one another by a link 425. Link 425 is typically a flexible link.

Various factors such as bulk, convenience of operation, and type of application, are used to determine the division of the components of contamination detector 100 between the two units. For example, in one application, base unit 420 is configured to house certain bulky components such as, for example, a power supply, a gas pressure regulator, and an optical spectrometer. Link 425 carries various items between the two units. Such items include, for example, electrical signals, optical signals, and gas.

Figure 5:
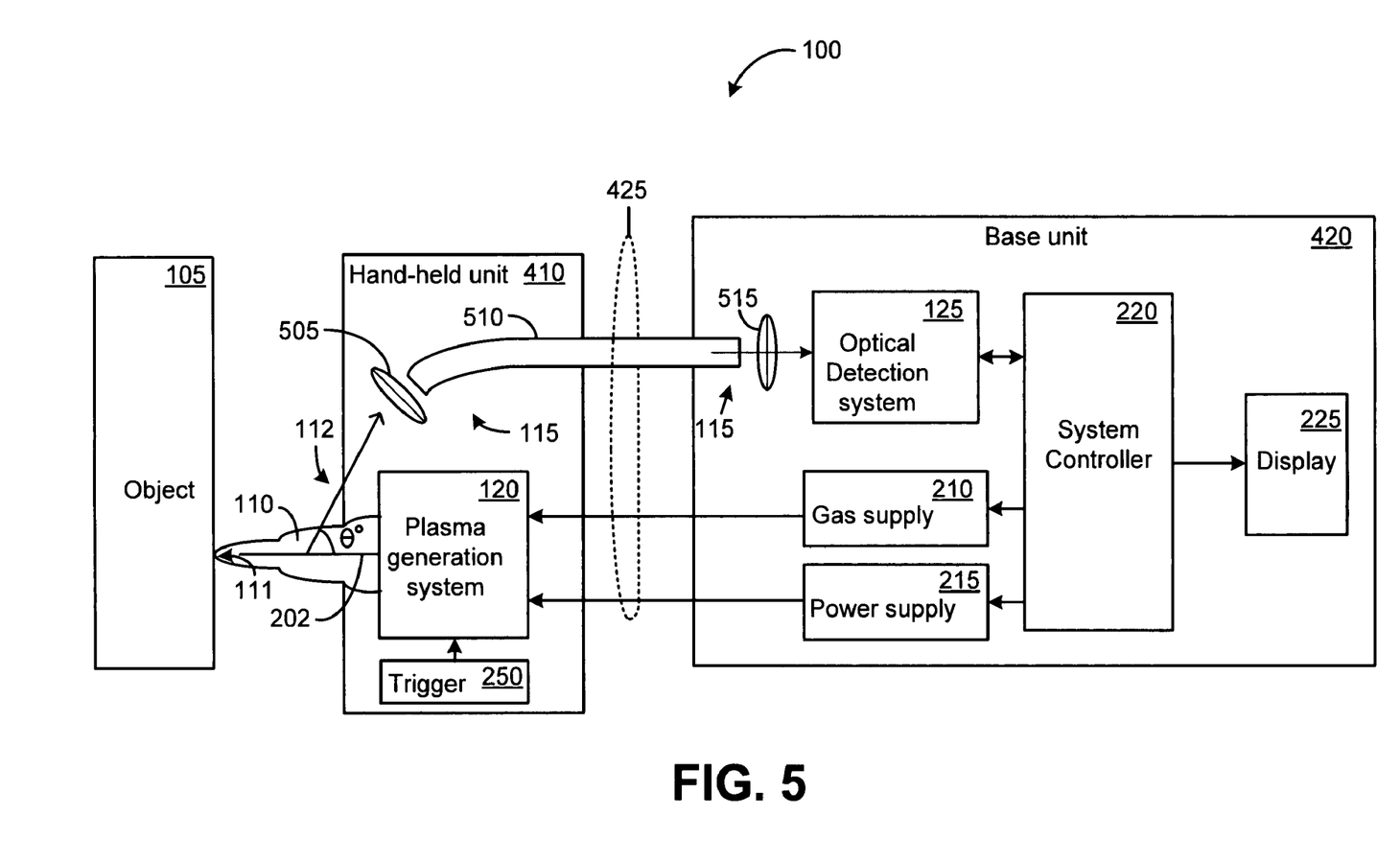
FIG. 5 is a block diagram showing one exemplary embodiment where certain components of the contamination detector are housed in the hand-held unit and remaining components housed in the base unit.

FIG. 5 is a block diagram showing an exemplary embodiment in which certain components of contamination detector 100 are housed in hand-held unit 410 with remaining components housed in base unit 420. In this embodiment, hand-held unit 410 houses at least a portion of plasma generation system 120, trigger 250, and some components of light capture system 115. Plasma generation system 120 includes, for example, a pair of electrodes for generating a micro-discharge in a stream of gas. Light capture system 115 includes some optical components such as, but not limited to, a lens 505 and an optical fiber 510.

Base unit 420 houses optical detection system 125, a portion of light capture system 115, gas supply 210, power supply 215, system controller 220, and display 225. The portion of light capture system 115 that is housed in base unit 420 includes a lens 515 and a part of optical fiber 510.

Other non-limiting examples of the optical components of light capture system 115 that may be optionally housed in either hand-held unit 410 or base unit 420 include: an optical conductor such as an optical waveguide or an optical fiber, a light directing element such as a mirror or a prism, and a light processing element such as an optical grating or an optical filter.

Figure 6:
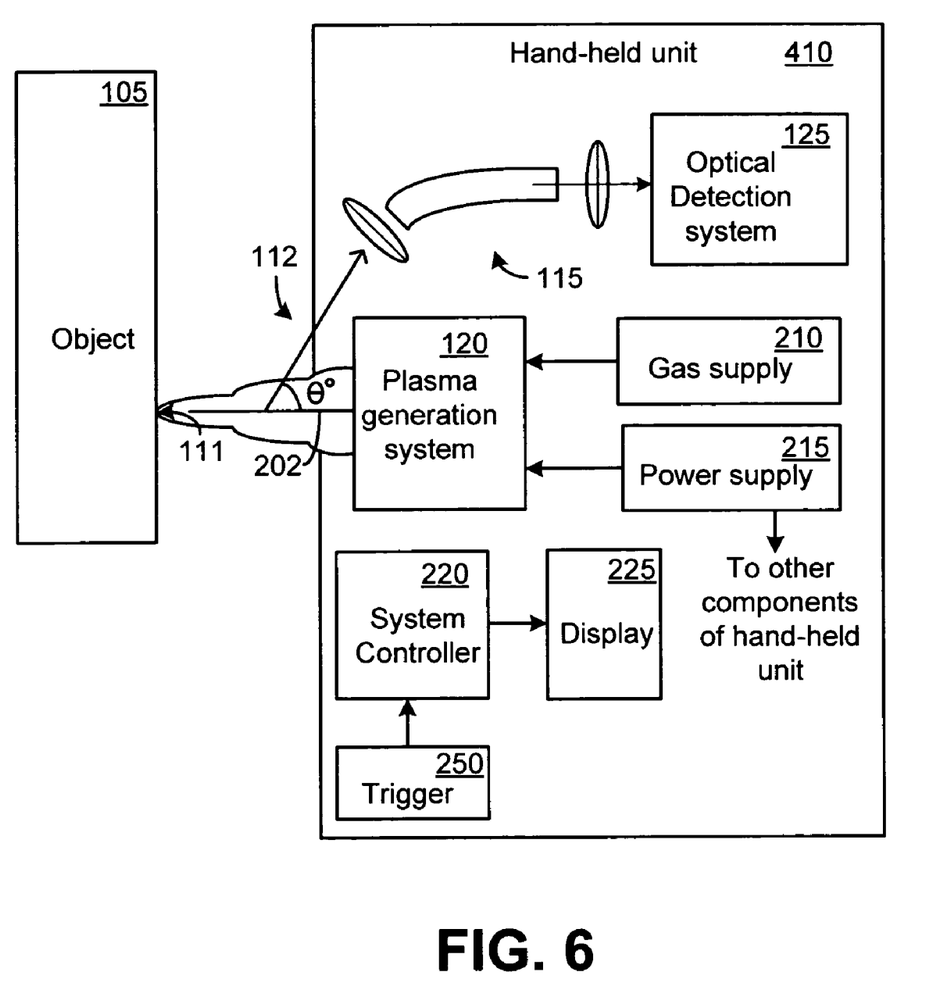
FIG. 6 is a block diagram showing another exemplary embodiment where the contamination detector is wholly housed in the hand-held unit.

FIG. 6 is a block diagram showing another exemplary embodiment in which contamination detector 100 is wholly housed in a hand-held unit 410. The exemplary embodiments shown in FIGS. 5 and 6 have light capture axis 112 extending non-parallel to longitudinal axis 202 of the atmospheric plasma discharge 110. In alternative embodiments the two axes may be parallel to and offset from one another.

Figure 7:
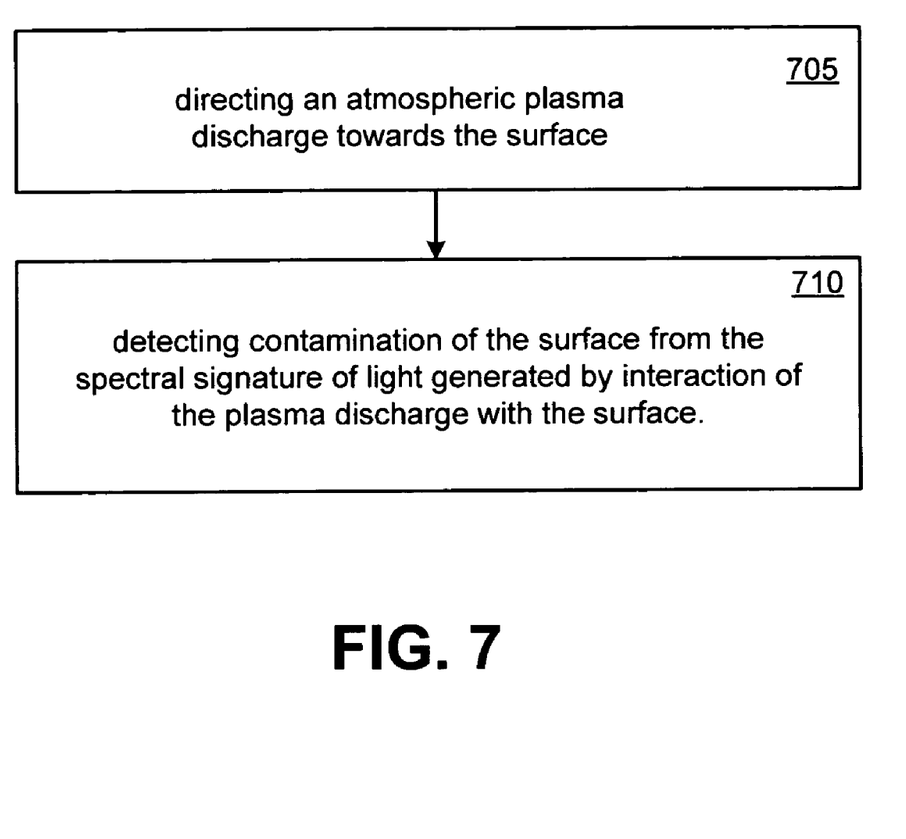
FIG. 7 is a flowchart showing an exemplary method for detecting contamination of a surface.

FIG. 7 is a flowchart showing an exemplary method for detecting contamination of a surface. In block 705 an atmospheric plasma discharge is directed towards the surface. In block 710, contamination of the surface is detected from the spectral signature of light generated by the interaction of the atmospheric plasma discharge with the surface. This process encompasses capturing the light generated by the interaction and using the spectral signature of the light to detect one or more contaminants. The detection process can be implemented in several alternative ways, some of which have been described above, for example, with reference to FIG. 2. A few additional exemplary methods will now be described.

In one such method, a reference spectral signature is used in conjunction with the spectral signature of the captured light to detect contamination of a surface under test. Different types of reference spectral signatures may be generated using several alternative methods, some of which are employed as a part of a calibration process for the contamination detector.

The first type of reference spectral signature is referred to in this disclosure as a null spectral signature. In a first exemplary method for generating the null spectral signature, the hand-held contamination detector is operated to direct a plasma discharge into free space at a location sufficiently far from the surface under test for the spectral signature to be unaffected by any contaminant that may be present on the surface. The resulting light is captured and routed to the optical spectrometer of the hand-held contamination detector. The optical spectrometer stores data representing the spectrum of the light as the null spectral signature. The null spectral signature is then used as a base-line reference in conjunction with the spectral signature of the light obtained when the hand-held contamination detector is directed towards the surface under test to detect contamination of the surface. In one exemplary method, the null spectral signature is subtracted from the captured spectral signature thereby resulting in the isolation of certain wavelengths that identify one or more contaminants.

The null spectral signature may be alternatively generated using a reference surface rather than free space. The reference surface is selected to correspond to the surface under test. For example, if the surface under test is metallic, the reference surface is also metallic. Similarly, if the surface under test is organic, the reference surface is also organic. The selected reference surface is cleaned free of contaminants, especially certain contaminants of interest. For example, if the contaminant of interest is a specific petroleum compound, the reference surface is thoroughly cleaned so as to remove any trace of this and other petroleum compounds. The hand-held contamination detector is operated to direct a plasma discharge towards the reference surface. The resulting light is captured and routed to the optical spectrometer of the hand-held contamination detector. The optical spectrometer stores data representing the spectrum of the light as the null spectral signature. The null spectral signature of the light is then used as a base-line reference in conjunction with the spectral signature of the light obtained when the hand-held contamination detector is directed towards the surface under test, to detect contamination of the surface. Here again, the null spectral signature may be subtracted from the captured spectral signature to isolate certain wavelengths that identify one or more contaminants.

The second type of reference spectral signature is referred to in this disclosure as a template spectral signature. In a first exemplary method for generating the template spectral signature, a controlled reference space is used. The controlled reference space is a controlled space containing a specific component related to a contaminant of interest that may be present on the surface under test. For example, when the contaminant of interest is an organic contaminant, the controlled reference space is configured to contain a known amount of carbon dioxide. The controlled reference space is further configured to be located sufficiently far from the surface under test for the spectral signature to be unaffected by any contaminant that may be present on the surface under test.

The hand-held contamination detector is operated to direct a plasma discharge into the controlled reference space. The resulting light is captured and routed to the optical spectrometer of the hand-held contamination detector. The optical spectrometer stores data representing the spectrum of the captured light as the template spectral signature. The template spectral signature is then used as a reference template for comparison with the spectral signature of the light obtained when the hand-held contamination detector is directed towards the surface under test to detect contamination of the surface. The comparison process typically involves matching the two signatures thereby providing an identification of certain wavelengths associated with the contaminant.

In a second exemplary method for generating the template spectral signature, a controlled reference surface is used. The controlled reference surface is created from a contaminant-free reference surface, which is selected to correspond to the surface under test. For example, if the surface under test is metallic, the contaminant-free reference surface is also metallic. Similarly, if the surface under test is organic, the contaminant-free reference surface is also organic. The controlled reference surface is created by depositing a specific amount of a contaminant of interest upon the contaminant-free reference surface. For example, a known amount of a silicone contaminant may be deposited on the reference surface to create the controlled reference surface. The controlled reference surface is further configured to be located sufficiently far from the surface under test for the spectral signature to be unaffected by any contaminant that may be present on the surface under test.

The hand-held contamination detector is operated to direct a plasma discharge towards the controlled reference surface. The resulting light is captured and routed to the optical spectrometer of the hand-held contamination detector. The optical spectrometer stores data representing the spectrum of the light as the template spectral signature. The template spectral signature is then used as a reference template for comparison with the spectral signature of the light obtained when the hand-held contamination detector is directed towards the surface under test, to detect contamination of the surface.

In an alternative embodiment, a combination of the template spectral signature and the null spectral signature described above is used in conjunction with the captured spectral signature to detect contamination of a surface under test. In this alternative embodiment, the null spectral signature is first obtained using the contaminant-free reference surface. The controlled reference surface is then created by depositing a specific amount of a contaminant of interest upon the contaminant-free reference surface. The template spectral signature is then obtained by directing the plasma discharge towards the controlled reference surface. Once the null spectral signature and the template spectral signature have been obtained, a residual reference spectral signature is generated by subtracting the null spectral signature from the template spectral signature.

The hand-held contamination detector is then directed towards the surface under test and the spectral signature of the resulting light is captured. The captured spectral signature and the null spectral signature are used to generate a residual spectral signature. This is carried out by subtracting the null spectral signature from the captured spectral signature. The residual spectral signature is then compared with the residual reference spectral signature to detect the contaminant of interest.

The above-described embodiments are merely set forth for a clear understanding of the principles of the disclosure. Many variations and modifications may be made without departing substantially from the disclosure. All such modifications and variations are included herein within the scope of this disclosure.

We claim:

1. A contamination detector, comprising:
   a plasma generation system operable to expel an atmospheric plasma discharge from said plasma generation system and direct the atmospheric plasma discharge towards a surface;
   an optical detection system configured to detect a contaminant; and
   a light capture system configured to capture light generated by interaction of the atmospheric plasma discharge with the surface and to guide the light to the optical detection system for detection;
   wherein said discharge is created within said plasma generation system and is independent of said surface.

2. A contamination detector, comprising:
   a plasma generation system operable to direct an atmospheric plasma discharge towards a surface;
   an optical detection system configured to detect a contaminant; and
   a light capture system configured to capture light generated by interaction of the atmospheric plasma discharge with the surface and to guide the light to the optical detection system for detection wherein the atmospheric plasma discharge is a micro-discharge and the light capture system is configured to capture light from a region close to the surface.

3. The contamination detector of claim 2, wherein the light capture system comprises an optical conductor having a light capture axis that is coincident with a longitudinal axis of the micro-discharge.

4. The contamination detector of claim 2, wherein the light capture system comprises an optical conductor having a light capture axis non-parallel to a longitudinal axis of the micro-discharge.

5. The contamination detector of claim 2, wherein the light capture system comprises an optical element from the group consisting of: an optical fiber, an optical focusing element, an optical waveguide, a mirror, an optical grating, and an optical filter.

6. The contamination detector of claim 2, additionally comprising a hand-held enclosure, the hand-held enclosure housing at least a portion of at least one of the plasma generation system, the light capture system, and the optical detection system.

7. The contamination detector of claim 2, wherein the light capture system comprises a light focusing system configured to capture light from a selected region in the region close to the surface.

8. The contamination detector of claim 7, wherein the selected region is located inside the micro-discharge.

9. A method for detecting contamination of a surface, the method comprising:
   generating an atmospheric plasma discharge within a plasma generation system;
   expelling the atmospheric plasma discharge from the plasma generation system;
   directing the atmospheric plasma discharge towards the surface; and
   detecting contamination of the surface from the spectral signature of light generated by interaction of the atmospheric plasma discharge with the surface.

10. The method of claim 9, further comprising:
    generating a null spectral signature, by directing the atmospheric plasma discharge towards a region free of any contaminant of interest.

11. The method of claim 10, wherein generating the null spectral signature comprises:
    directing an atmospheric plasma discharge into free space; and
    obtaining the null spectral signature from light generated by the atmospheric plasma discharge into free space.

12. The method of claim 10, wherein generating the null spectral signature comprises:
    directing an atmospheric plasma discharge towards a reference surface; and
    obtaining the null spectral signature from light generated by interaction of the atmospheric plasma discharge with the reference surface.

13. The method of claim 9, further comprising:
    generating a template spectral signature, by directing the atmospheric plasma discharge towards a region containing a component related to a contaminant of interest.

14. The method of claim 13, wherein generating the template spectral signature comprises:
    directing an atmospheric plasma discharge into a controlled reference space; and
    obtaining the template spectral signature from light generated by the atmospheric plasma discharge into the controlled reference space.

15. The method of claim 13, wherein generating the template spectral signature comprises:
    directing an atmospheric plasma discharge towards a controlled reference surface; and
    obtaining the template spectral signature from light generated by interaction of the atmospheric plasma discharge with the controlled reference surface.

16. The method of claim 9, further comprising:
    using a gas to generate the atmospheric plasma discharge.

17. A method comprising:
    providing a hand-held contamination detector comprising an enclosure,
    generating an atmospheric plasma discharge within the enclosure;
    expelling the atmospheric plasma discharge out of the enclosure;
    directing the atmospheric plasma discharge towards a surface using the hand-held contamination detector;
    using the hand-held contamination detector to capture the spectral signature of light generated by interaction of the atmospheric plasma discharge with the surface; and
    detecting contamination of the surface from the spectral signature.

18. The method of claim 17, in which the directing comprises generating the atmospheric plasma discharge using a gas.

19. The method of claim 17, in which:
    the method additionally comprises:
    directing the atmospheric plasma discharge towards a reference surface free of any contaminant of interest; and
    using the hand-held contamination detector to capture a null spectral signature generated by interaction of the atmospheric plasma discharge with the reference surface; and
    the detecting comprises detecting the contamination of the surface from the spectral signature and the null spectral signature.

20. The method of claim 17, in which:
    the method additionally comprises:
    directing the atmospheric plasma discharge towards a controlled reference surface containing a component related to a contaminant of interest; and
    using the hand-held contamination detector to capture a template spectral signature generated by interaction of the atmospheric plasma discharge with the controlled reference surface; and
    the detecting comprises detecting the contamination of the surface from the spectral signature and the template spectral signature.

* * * * *